United States Patent [19]
Mahoney et al.

[11] Patent Number: 5,914,124
[45] Date of Patent: Jun. 22, 1999

[54] ALGINATE FIBRE, PROCESS FOR THE PREPARATION THEREOF AND USE

[75] Inventors: Peter M. J. Mahoney, Powys; David Pritchard, South Glamorgan; Anne Elizabeth Howells, West Glamorgan; Bryan Griffiths, Gwent, all of United Kingdom

[73] Assignee: Bristol-Myers Squibb Company, New York, N.Y.

[21] Appl. No.: 08/765,748

[22] PCT Filed: Jul. 14, 1995

[86] PCT No.: PCT/EP95/02773

§ 371 Date: May 30, 1997

§ 102(e) Date: May 30, 1997

[87] PCT Pub. No.: WO96/02284

PCT Pub. Date: Feb. 1, 1996

[30] Foreign Application Priority Data

Jul. 15, 1994 [GB] United Kingdom .................... 9414305

[51] Int. Cl.$^6$ ....................................................... A61F 13/00
[52] U.S. Cl. ........................... 424/443; 424/445; 424/484; 424/488; 424/DIG. 13
[58] Field of Search ...................................... 424/443, 445, 424/484, 488, DIG. 13

[56] References Cited

U.S. PATENT DOCUMENTS 5,690,955  11/1997  Griffiths .................................. 424/443

FOREIGN PATENT DOCUMENTS

92/22285  12/1992  WIPO .............................. A61K 9/07
94/17227   8/1994  WIPO .............................. D01F 9/04

*Primary Examiner*—D. Gabrielle Brouillette
*Attorney, Agent, or Firm*—John M. Kilcoyne; Theodore R. Furman, Jr.

[57] ABSTRACT

Alginate fibres comprising at least one medicament incorporated into the structure thereof, the medicament being present at a level of at least 10% by weight, based on the weight of the alginate fibre with no incorporated medicament.

19 Claims, 6 Drawing Sheets

FIG. 1 TGA

ALGINATE FIBRE, PROCESS FOR THE PREPARATION THEREOF AND USE

This application is a 371 of PCT/EP95/02773, filed Jul. 14, 1995.

The present invention relates to alginate fibre, and more particularly to a medicament-impregnated alginate fibre. The invention concerns a fibre from which medicament can be released in a controlled manner, and to the application of this fibre in the preparation of alginate fabrics and wound dressings.

A number of methods for producing conventional alginate fibres are described in the art. The extrusion of alginate solutions into an aqueous solution containing calcium ions to form yarns of calcium alginate filaments is known, for example, from British Patents Nos. 567641, 568177, 571657 and 624987. Such fabrics were generally prepared by knitting a yarn of calcium alginate filaments and partially converting the calcium alginate to the sodium form to form a calcium/sodium alginate containing, for example, 30–70 percent by weight of the carboxyl groups of the alginate in the calcium form.

The use of alginate fibres in the preparation of wound dressings which may incorporate certain medicaments is also known in the art. For example, EP-A-0279118 describes an adhesive product suitable for use on wounds comprising a backing layer of a moisture vapour transmitting continuous polymer film and a layer of a pressure sensitive adhesive containing inter alia at least 30% by weight of alginate. The adhesive product described therein can contain a medicament, such as a chlorhexidine derivative, normally in the adhesive layer. Alternatively, the medicament may form part of the alginate polymer used for the pressure sensitive adhesive layer, suitable examples being stated to include silver, copper and zinc derivatives of sodium alginate.

Additionally, U.S. Pat. No. 4,753,231 discloses the incorporation of such antibacterial agents as silver sulphadiazine, povidone-iodine, chlorhexidine salts such as gluconate, acetate and hydrochloride, and quaternary agents such as benzalkonium chloride into a wound dressing pad.

Moreover, U.S. Pat. No. 4,817,594 discloses wound dressings as supports for therapeutic or antiseptic materials including iodine, formol, lime, oxygen, bacillary toxins and the like.

The commercially available products Bactigras and Serotulle, obtainable respectively from Smith and Nephew Ltd., Hull, United Kingdom, and Seton Healthcare Group, Oldham, United Kingdom, both consist of paraffin gauze impregnated with the antibacterial agent chlorhexidine.

The abovedescribed medicated wound dressings of the prior art comprise medicaments absorbed onto the surface of the fibres making up the wound dressing. The use of such wound dressings is somewhat restricted by the amount of medicament which can be incorporated onto the surface of the alginate fibre, and furthermore by the fact that such surface-bound medicaments are expected to be released rapidly in the environment of use. For a variety of clinical applications, it is considered desirable to provide a controlled release of the same or a different medicament to a wound over time. If the medicament were merely applied topically throughout the treatment regimen, this would require frequent removal and replacement of the dressing, with concomitant inconvenience and risk of opportunistic infection.

WO 94/00164 describes an alginate fibre comprising one or more medicaments incorporated into the fibre core such that the or each medicament can be released in a sustained manner over time, and optionally one or more medicaments which can be attached to the surface of the fibre for rapid release therefrom. The amount of medicament which can be incorporated onto the surface and/or into the core is respectively 0.01% to 2.0% by weight.

We have now developed alginate fibres which allow increased incorporation of one or more medicaments into the structure thereof, the medicament thereby being suitable for sustained release from the alginate fibre.

According to the present invention there is provided alginate fibre comprising at least one medicament incorporated into the structure thereof, the medicament being present at a level of at least 10% by weight, based on the weight of the alginate fibre with no incorporated medicament.

Skilled researchers will appreciate that the incorporation of the medicament in the structure of the alginate fibre at the above described level is extremely surprising and advantageous, in view of the hitherto known lesser incorporation of 0.01% to 2.0% by weight. The increased level of medicament incorporated into the structure of the fibre allows the sustained release of the medicament over a longer period of time.

Furthermore, in the case where the fibre is employed as a wound dressing, the abovementioned increased level of medicament incorporation will reduce the frequency of removal and replacement thereof relative to a wound environment.

Favourably the medicament is present in the alginate fibres at a level of at least 20% by weight, based on the weight of the alginate fibre, preferably at least 40% and even more preferably at a level of at least 60% by weight, based on the weight of the alginate fibre. Surprisingly it has been found that the medicament may suitably be incorporated into the fibre in an amount of up to 100% by weight, based on the weight of the original fibre. (Such figures are also provided for various embodiments of the invention described hereinafter).

Suitable medicaments for use in conjunction with the alginate fibre according to the invention include antibacterial agents, for example bisbiguanide derivatives such as chlorhexidine, both in the free base form and as the acetate, gluconate or hydrochloride salts; nisin, a polypeptide available in nature from various strains of the bacterium Streptococcus lactis; oxytetracycline and tetracycline itself; sulphonamide derivatives such as sulphadiazine; antiprotozoal agents, for example imidazole derivatives such as metronidazole; antifungal agents such as chlorphenesin; phenothiazine derivatives such as promethazine and chlorpromazine; nucleosides such as iodouridine; hormones such as noradrenalin, insulin, growth hormones, secretin, vasopressin, substance P and the like; proteases, such as streptokinase, streptodornase and the like, as debriding agents; antibiotics, such as gentamycin sulphate and the like; and anti-inflammatory agents, for example steroid derivatives such as hydrocortisone and prednisolone, angiogenisis promoting agents and the like.

Alginate fibre according to the present invention are particularly suitable for use as a wound dressing, and there is provided by the present invention a wound dressing formed in whole or in part from alginate fibre comprising at least one medicament incorporated into the structure thereof, the medicament being present at a weight of at least 10% by weight, based on the weight of the fibre.

Suitably the wound dressings according to the present invention comprise pads of algiante fibre and most aptly the pad is 0.5 to 7.5 mm thick and is preferably 1 to 5 mm thick, for example 1.5 to 3 mm thick. Typical pad sizes are rectangular with sides of from 4 to 20 cm, for example 5 to 15 cm, 10×10 cm and the like although other shapes may be employed such as circular, oval or the like.

A wound dressing according to the present invention may also comprise one or more further absorbent layers. Suitably, the wound dressing may include one or more absorbent layers arranged on either side of alginate fibre according to the present invention.

Suitably the further absorbent layer or layers is selected from the group consisting of alginate fibres, karaya gum, locust bean gum, guar gum, sodium acrylate, polyvinyl alcohol, pectin, gelatin, carboxymethylcellulose, high molecular weight carbowaxes, carboxy polymethyl collagen and cotton.

Aptly the absorbent layer comprises alginate fibres. Alginates are produced by a variety of micro-organisms and marine algae which are the normal commercial source. The alginates being natural materials show considerable variety but are characterised in being block copolymers, the individual monosaccheride units being arranged into groups as blocks of mannuronic (M) and guluronic (G) residues. In addition to the repeating blocks each polymer chain can contain a proportion of alternating M and G monosaccharide units.

Suitably alginate fibres employed in the absorbent layer may be high M or high G, typically 60–80% by weight M or G respectively. The alginate fibres may be high absorbent fibres provided by step (1) to (4) of a process substantially as hereinbefore described.

The alginate fibres of the further absorbent layer or layers may, for example, be non-woven, woven or knitted. Preferably, the fabric is non-woven, not only from the standpoint of ease of manufacture but also because of the general dimensional stability of non-woven fabrics, which are acknowledged not to stretch so easily as, for example, knitted fabrics.

In the preparation of a non-woven fabric, a cotton card may be used to form a web, which may then be cross-lapped, for example with a Garnet Bywater cross-lapper, and then needle punched in a Garnet Bywater needle loom. In the preparation of a woven fabric, the precursor alginate fibres may be carded and then spun into a yarn, which can be woven in a conventional loom. Alternatively, the fibres may be collected in a spinning box, according to the method described in British Patent No. 568177, and woven. In the preparation of a knitted fabric, the fibres can be prepared as a continuous filament yarn/ again according to the method described in British Patent No. 568177, which is then knitted on a conventional knitting machine.

The wound dressing according to the present invention may further be provided with a film layer suitably comprising a moisture vapour permeable film for example a polyurethane, polyetherester or a polyether amide. Aptly such films will be from 15 to 50 microns thick, more usually 20 to 30 microns, for example 25 microns. The film layer may be applied directly to the surface of the alginate pad but more suitably will be adhered by means of an adhesive, for example as described in WO 90/01954 or EP 0 279 118. Such adhesives are preferably moisture vapour permeable, for example an acrylic, polyurethane or polyether adhesive of which acrylic adhesives are preferred.

The wound dressings formed from the alginate fibre according to the present invention will advantageously be conventional dressings well known in the art. Examples of suitable dressings include bandages, adhesive strip dressings, island dressings, pads of various kinds, surgical sponges and packs and ward dressings. Such dressings may conveniently be prepared by standard methods known from the art.

The fibres and dressings in accordance with the present invention will conveniently be packaged in an hermetically-sealed envelope and sterilised, e.g. with ethylene oxide or by irradiation using gamma rays or an electron beam.

In the case where the alginate fibres are to be employed as a wound dressing, favoured medicaments include proteases, such as streptokinase, streptodornase and the like, wherein the proteases are employmed as debriding agents in the breakdown of hard eschar. In this way, subsequent uptake of the solubilised eschar, associated toxins and the like, into the same, or a subsequently applied dressing, can be acheived.

In the case where the alginate fibres are employed as a wound dressing, the fibres are advantageously employed in a wetted state so as to acheive efficient release of the medicament to the wound environment.

There is further provided by the present invention a method of treating a wound, which method comprises applying a wound dressing comprising alginate fibre to a wound environment, the fibre comprising at least one medicament incorporated into the structure thereof, the medicament being present at a level of at least 10% by weight, based on the weight of the fibre.

As hereinbefore described the method advantageously comprisese wetting the alginate fibre. Wetting of the alginate fibre can either be achieved in situ when the dressing is applied to a wound environment by uptake of exudate from the wound or the fibres may be wetted prior to application to the wound environment.

Suitably the fibre may be wetted either with pure water or preferably with saline solution. The high water retention capability of the fibres will ensure that an appreciable supply of water is available from the wetted fibres, to the wound environment. A further advantage of the fibres is that they do not drip when applied to a curved surface such as an area of the human body, in contrast to conventional dressings such as surgical gauze and cotton wool which have a propensity to allow water to "run off".

The fibres may suitably be supplied in a pre-wetted state, or alternatively may be supplied in the dry state with instructions for wetting before application to a wound environment. If supplied in a pre-wetted state, the fibres will advantageously incorporate conventional preservatives, for example Metasol D3T (Merck), Parasept (methyl paraben) (Kaloma Chemical) or Bromopol (2-bromo-2-nitro-1,3-propanediol) (Boots Ltd.), in order to prevent or retard the biological degradation of the fibre constituents.

Suitably a method according to the present invention involves applying alginate fibres to a wound environment for a period selected from one to sixteen days, depending on the acuteness of the wound and the recovery observed. In the case of a rapidly healing, relatively non-acute wound the method involves applying the fibres to a wound environment for one to two days. Alternatively, in the case of an acute wound, such as a heavily exuding ulcer or burn, the method according to the present invention comprises applying the alginate fibres to the wound environment for up to sixteen days.

Aptly a method according to the present invention involves removal of the fibres from the wound environment undergoing treatment on a once or twice daily basis. Aptly removal of the fibres involves irrigation with pure water or saline solution and may further comprise excision of the slough or eschar, by for example removal of the top layer of the slough or eschar.

Alginate fibres according to the present invention are also suitable for use in implantation compositions required to have a high level of medicaments incorporated therein. Suitable implantation compositions include bioerodible drug delivery systems, which may be in a pad or sliver form. Most aptly the pad is 0.5 to 7.5 mm thick and is preferably 1 to 5 mm thick, for example 1.5 to 3 mm thick. Typical swab sizes are rectangular with sides of from 4 to 20 cm, for example 5 to 15 cm, 10×10 cm and the like although other shapes may be employed such as circular, oval or the like. The sliver is typically of 3 to 5 mm in diameter and 10 to 20 cm in length and typically erode over a time period of 1 to 2 weeks, 5 to 7 weeks and three to four months in respective cases where solubilising, solubilising/insolubilising and insolubilising ions are employed.

Aptly the drug delivery system includes an antibiotic, such as gentamycin sulphate, and in an advantageous application of the present invention the delivery system, in the form of a pad or sliver, is employed at a site of infection, often in a case where part of a patient's bone has been removed. A further advantageous application of the present invention is in dental treatment, wherein aptly a sliver of alginate fibre as hereinbefore described is administered to a treatment site in a patient's mouth. In this latter application a preferred medicament comprises an antiprotozoal agent such as metronidazole.

Suitably the implantation compositions include alginate fibres having a mid or high guluronic acid content, by which is meant the fibres comprise 50 to 80% by weight guluronic acid so as to reduce the non-immunogenic properties of the implantation compositions.

The time taken for substantially all of the medicament or medicaments incorporated into the fibre structure to be released will depend on such factors as the nature of the medicament or medicaments used, the amount of medicament(s) used, and the permeability of the alginate fibre. Different release periods will be required for different clinical situations. Typically the or each medicament will be released into the environment of use over a period of hours, days or weeks. In the case of a wound dressing which as hereinbefore described is suitably removed from a wound environment the release of the medicament typically occurs over a period of hours, such as 6 to 10 hours. In the case of an implanation composition employing alginate fibre according to the present invention, the medicament is suitably released from the structure of the fibre over a period of days or weeks.

The alginate fibres according to the invention may be characterised by reference to their unique thermal properties, in that a plot of the first order derivative of percentage weight loss of the fibre with temperature against temperature has two maxima in the range of 100 to 400° C.

In general, the two maxima in the plot of the first order derivative of percentage weight loss with temperature against temperature for a fibre according to the invention will fall within the range 200 to 300° C., preferably 220 to 290° C.

Thermogravimetric analysis was performed using a 2950TGA manufactured by TA Instruments, Delaware, U.S.A. Differential scanning calorimetry (DSC) was performed using a DSC7 manufactured by Perkin-Elmer.

Figure 1:
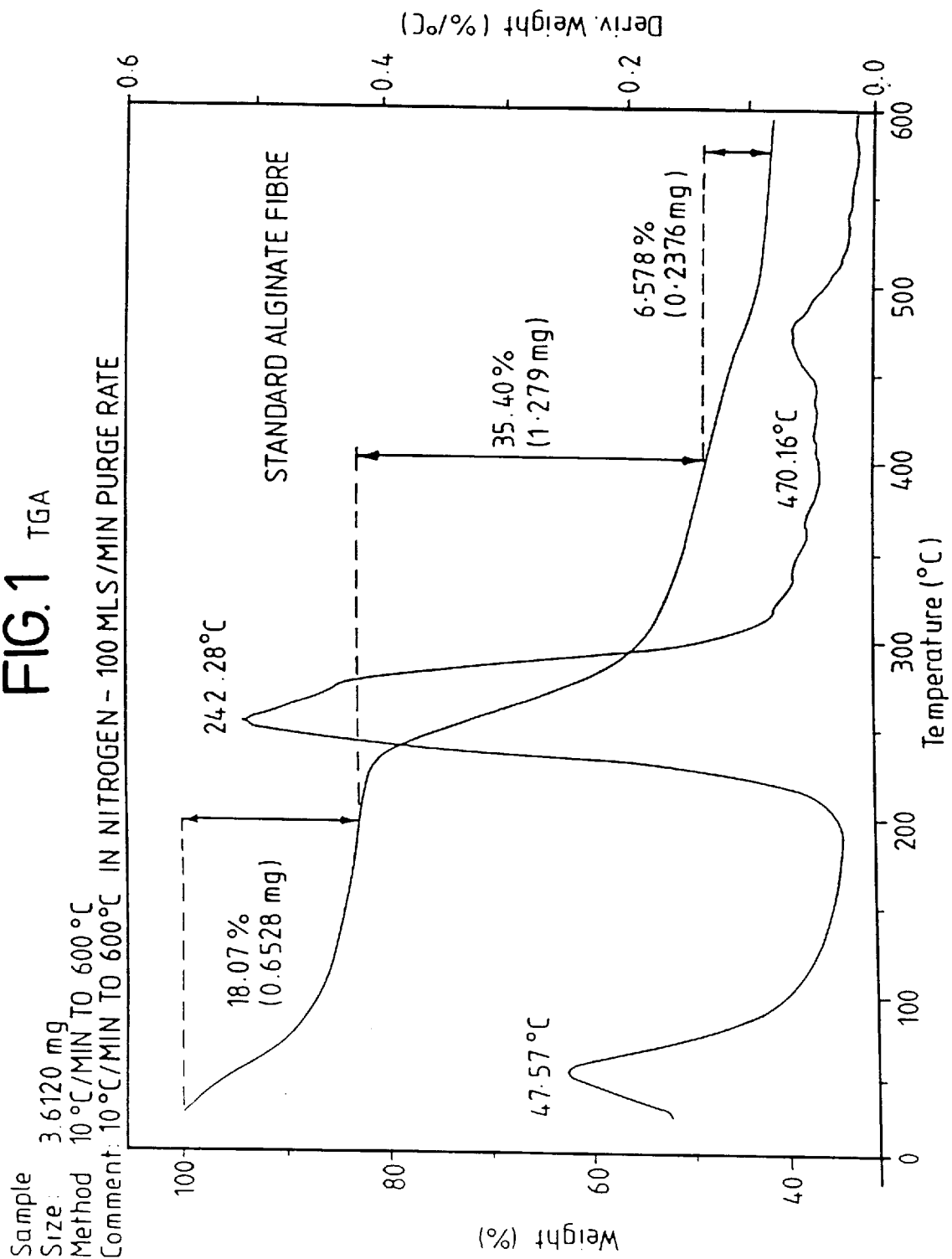
FIG. 1 shows the thermogravimetric analysis (TGA) of an 80:20 calcium:sodium alginate fibre prepared by conventional methods.
Figure 2:
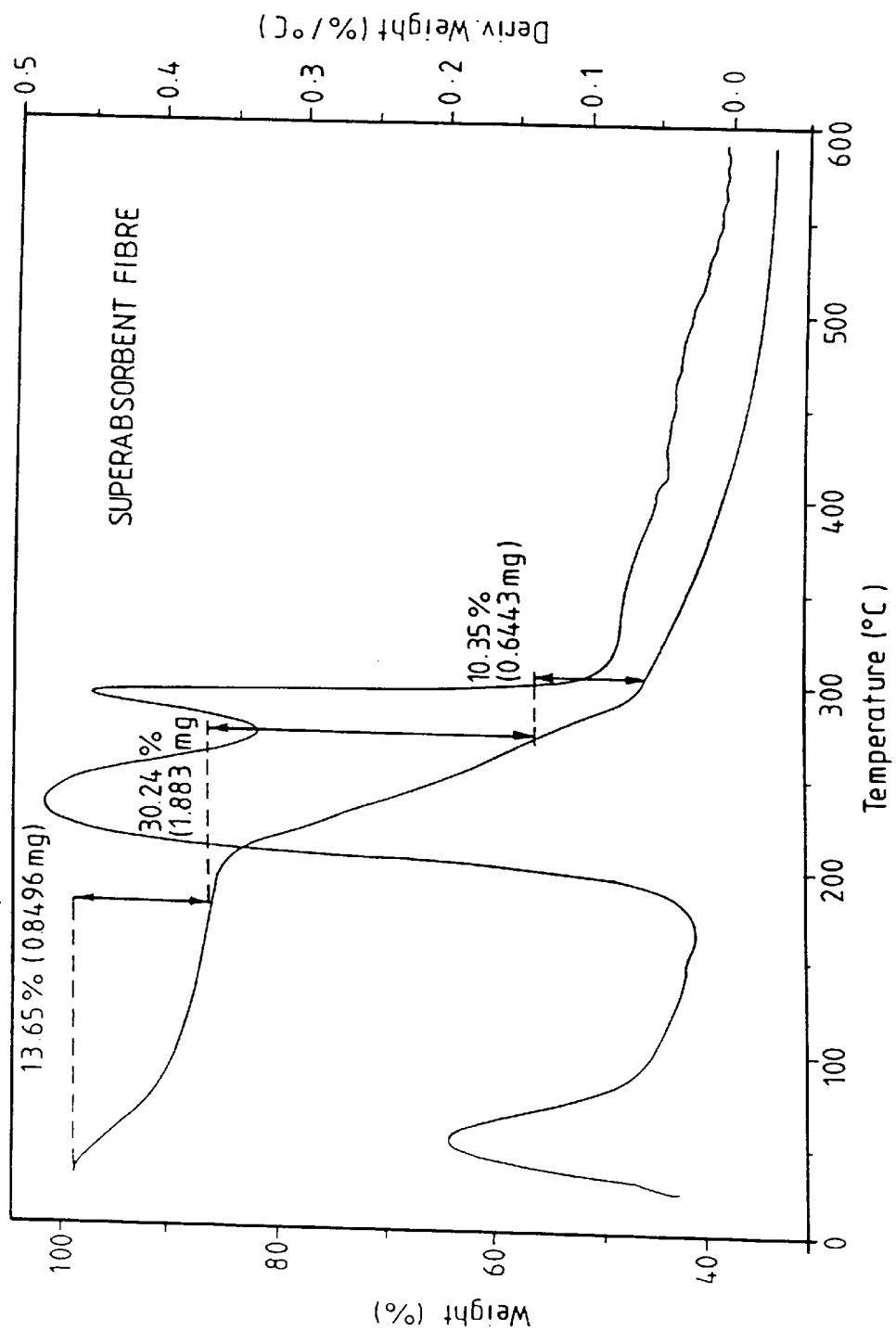
FIG. 2 shows the thermogravimetric analysis (TGA) of a fibre according to the invention, prepared from the same source material as the fibre of FIG. 1.

FIG. 1 shows the percentage weight loss of a conventional alginate fibre with increasing temperature, and the first order derivative of that function. The derivative shows a single maximum at approximately 240° C. In contrast, the first order derivative of percentage weight loss with temperature for a corresponding fibre according to the present invention, shown in FIG. 2, has two peaks, one at a lower temperature than the maximum observed for the conventional fibre (approximately 225° C.), and one at a higher temperature than the maximum observed for the conventional fibre (approximately 280° C.). This "splitting" of the derivative maximum for the conventional fibre of the same composition is characteristic of fibres according to the present invention.

Figure 3:
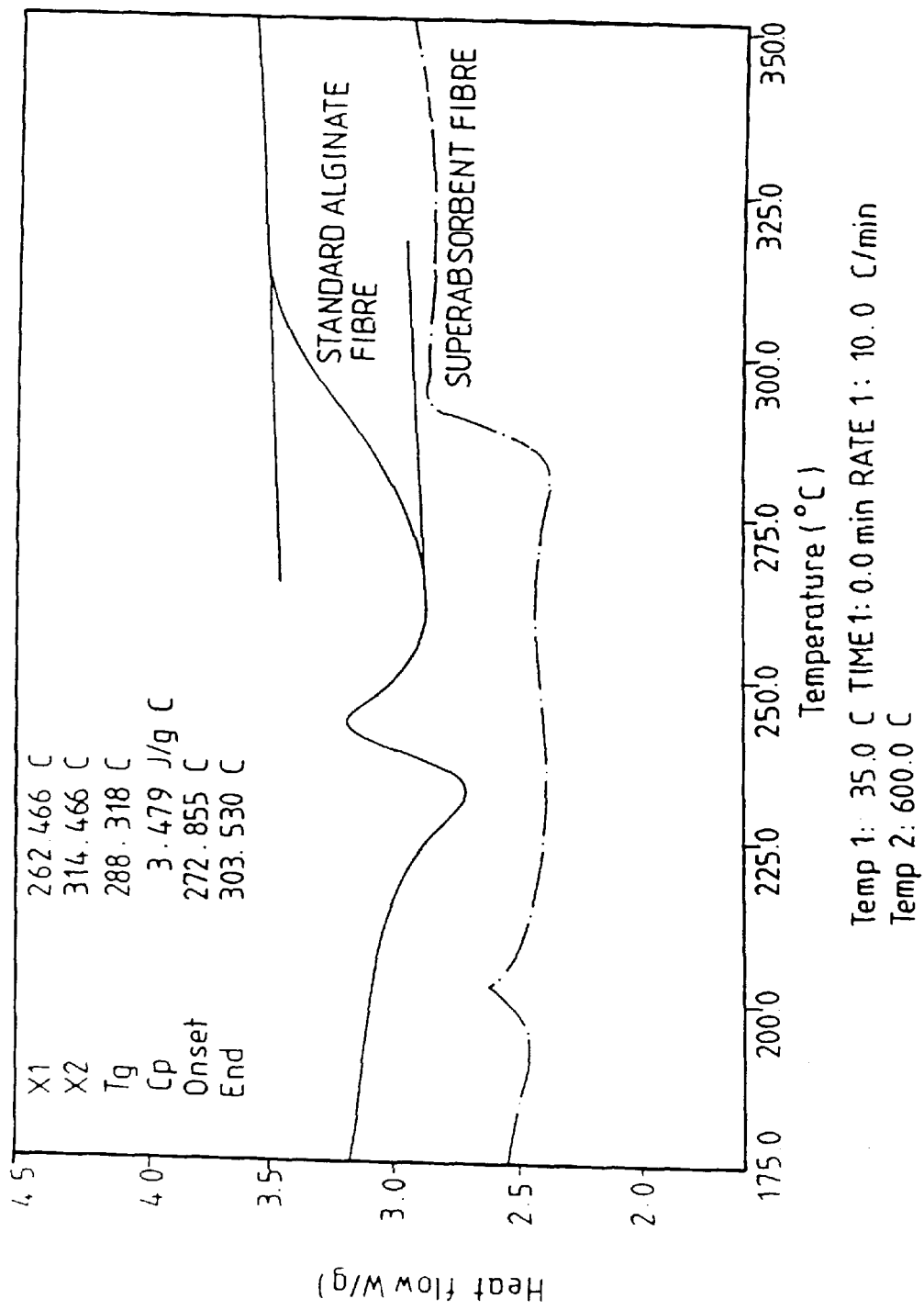
FIG. 3 shows the variation of heat flow with temperature for a conventional 80:20 calcium:sodium alginate fibre and a corresponding fibre in accordance with the present invention.

FIG. 3 also shows differences in the thermal properties of a conventional alginate fibre and a fibre according to the present invention. Heat flow is effectively a measure of enthalpy associated with a transition, reaction or decomposition. The glass transition termperature (Tg) shown in FIG. 3 is the same for both fibres (288° C.). However, it can be seen that the transition for the conventional fibre is broad, occuring over some 50° C., whereas that for the fibre in accordance with the invention is sharp, taking place over less than 20° C.

Thus, alginate fibre according to the present invention can be further characterised in that its glass transition range is less than 30° C., such as about 26° C.

Alginate fibres employed in fabrics according to the present invention can further be characterised in terms of their dielectric behaviour. For polymers the dielectric constant is dependent on the ease with which the polymer orientates itself in response to an applied field and this is a function of the structure of the polymer. The constant is most easily expressed in terms of the relationship between the in-phase and out-of-phase components of the dynamic field. This is conventionally expressed as Tanδ. Multiple peaks are normally recorded when measuring Tanδ due to a variety of relaxation phenomena. We have found that alginate fibres suitable for use in the fabrics of the present invention have Tanδ values in the range of less than 1 and up to 15 Hz. Conventional alginate fibres have Tanδ values of from 40 Hz to 7000 Hz.

Alginate fibres according to the invention may be prepared by the following steps:

(1) treating alginate fibres with a suitable acid so as to produce fibres comprising approximately 90–98%, such as 95%–98%, alginic acid fibres;

(2) treating the alginic acid fibres with a saturated aqueous solution of mono- or divalent cations;

(3) washing the fibres with water until imbibition of water by the fibres has effectively ceased;

(4) treating the fibres with a source of a cation capable of forming a water-soluble alginate salt.

The fibres used as starting material in step 1 may be conventional salted alginate fibres (for example sodium, calcium, mixed sodium/calcium fibres produced in conventional manner, for example from 2–10% w/w solutions, for example 4% solution)

Most suitably the alginate fibres for use in step (1) are calcium alginate fibres which can be spun from a dope solution of 2 to 8% by weight sodium alginate, suitably 4 to 6% by weight, employing techniques conventional to the art.

Suitable acids of use in step (1) include acids capable of protonating alginic acid and may include both organic and inorganic acids. Preferably, hydrochloric acid will be used. Preferably the resulting alginic acid fibres have at least 95% of the acid residues in the unsalted form.

Suitable mono- or divalent cations of use in step (2) include solutions of sodium, potassium and magnesium cations. Preferably a pharmaceutically acceptable monovalent cation is used, most preferably a sodium ion.

Step (3) is preferably effected by washing the fibres in a stream of deionised water. Desirably step (3) may be discontinued when swelling has ceased.

Cations capable of forming water-soluble alginate salts include, for example, sodium, potassium, lithium, ammonium and magnesium cations. Preferably the source of a cation capable of forming a water-soluble alginate salt used in step (4) is a source of sodium cations, more preferably sodium carbonate. Other carbonates may be used in like manner to produce the alternative salts.

Small quantities of other ions (for example zinc or silver) may be present in step (4) if desired but generally these may be included in the fibre after completion of step (4) if their presence is required.

A method of treating the product of the above process to include other ions is to treat the product with an aqueous solution of a source of the ions.

The fibres may be collected at the end of step (4) by filtration or other suitable method and may be dried, for example by treatment with acetone and then drying in air. It is one of the advantages of this invention that the highly absorbent fibres may be dried without losing their ability to be highly absorbent when rewetted.

Aptly the fibres have a staple length of 0.25 to 25 mm, more usually 0.5 to 15 mm, favourably 1 to 12 mm and preferably 1.5 to 10 mm.

The alginate may be obtained from any convenient source, for example L. Hyperbola or Eclonia Maxima of which Eclonia Maxima is preferred.

The fibres prepared according to the abovedescribed process may be dried using conventional methods, for example, using acetone or hot air drying.

In addition to the abovementioned medicaments, it has further been found that hyaluronic acid can be incorporated into fibres prepared as above.

Hyaluronic acid (hereinafter referred to as HA) is a natural high viscosity mucopolysaccharide, generally having a molecular weight range of $3 \times 10^3$ to $8 \times 10^6$ Daltons (although there are reports of HA having molecular weights as high as $13 \times 10^6$) depending on source, method of isolation and method of determination. The isolation and characterisation of HA are described in Meyer, et al., J. Biol. Chem. 107, 629, (1934); J. Biol. Chem. 114, 689, (1936); Balazs, Fed. Proc. 17, 1086, (1958); Laurent, et al., Biochem. Biophys. Acta. 42, 476, (1960); Weissman, et al., J. Am. Chem. Soc., 76, 1753, (1954); and Meyer, Fed. Proc. 17, 1075, (1958).

HA is normally employed as its sodium salt although some other salting ions such as potassium or calcium or the like may also be preesnt. All such physiologically acceptable forms and especially the sodium salt are encompassed within the term HA herein.

HA is frequently used in ocular surgery as a replacement for subretinal fluid and vitreous humor. HA can also be used as a replacement for synovial fluid that is lost as a result of surgery or chronic inflammatory disease such as rheumatoid arthritis. HA is also known to be implicated in wound healing and angiogenesis. A wound dressing capable of providing sustained release of hyaluronic acid might therefore be expected to promote wound healing and/or angiogenesis.

There are accordingly further provided fibres in accordance with the present invention additionally comprising hyaluronic acid.

A suitable average molecular weight range for HA for use in the fibres of the present invention is $1.5 \times 10^3$ to $2 \times 10^6$, such as $1 \times 10^4$ to $1 \times 10^6$, preferably $1.5 \times 10^4$ to $1 \times 10^5$, more preferably about $7.5 \times 10^4$.

It is believed that the HA incorporated into fibres of the invention resides in spaces or "pockets" in the internal structure of the fibre and that release of the HA from the fibre to the environment of use takes place in a sustained manner as the fibre swells under the conditions of use. For example, fibres according to the present invention containing HA may be formed into a fabric used to prepare a wound dressing. As the dressing absorbs wound exudate, the fibres swell and HA is delivered to the wound in a sustained manner.

Incorporation of HA into the fibres of the invention may be achieved by contacting fibres prepared as above with an aqueous solution of HA followed by a suitable aqueous ionic solution, such as a solution of calcium, magnesium or zinc cations, preferably a solution of calcium cations, more preferably aqueous calcium chloride solution.

Alginate fabric fibres collected following step (4) have considerably improved absorbency as compared to fibres prepared from conventional alginate fibres. More specifically, the absorbency of the fibres is at least 40.0 grams of deionised water per gram of fibre as measured with reference to the test method depicted in FIG. 4 appended hereto. The fibre therefore has an absorbency of at least 40 times its own weight of deionised water and more aptly at least 60 times and most aptly at least 80 times its own weight of deionised water. Typically the fibre has an absorbency of much greater than this, for example 80 to 280 times its own weight, such as about 120 grams of deionised water per gram of fibre.

The solubility of the fibres may be modified by choosing the degree of neutralisation of the unsalted carbonyl groups by solubilizing ion. Thus for example, if a sheet of fibres (such as may be employed in a dressing) is required which is highly absorbent but which will remain intact as gelled fibres, the fibres are produced under conditions where a small proportion of residual carboxy groups is retained (for example by using insufficient $Na_2CO_3$ or the like to effect complete neutralisation). Alternatively, the material can be made fully soluble by replacing essentially all of the unsalted carboxy groups with a solubilizing ion such as sodium (for example by using at least a sufficient amount of $Na_2CO_3$ or the like to effect complete neutralisation).

Aptly the alginate fibres according to the present invention comprise a mixed salt alginate which has first and second cations, the first cation being capable of forming an insoluble alginate salt and the second cation being capable of forming a soluble alginate salt. Suitably the first cation is calcium, although it will be appreciated that other cations such as zinc and the like could be employed. Typically the second cation comprises a solubilising cation such as sodium, potassium, lithium, ammonium, magnesium and the like, sodium being preferred.

Apt ratios of the first (insolubilising) to the second (solubilising) cations is in the range of 30:70% to 100:0% by weight. More suitably the ratio of insolbilising to solubilising cations is 70:30 to 100:0% by weight, and even more suitably 80:20 to 100:0% by weight.

A method of preparing fibres having a higher content of insolubilising cations, such as calcium, than those prepared directly by the process as described above which employs sufficient $Na_2CO_3$ is to treat the fibre with insolubilising ions, such as calcium ions, for example from a solution of calcium chloride or the like, so that some of the sodium ions are replaced by calcium ions.

A method of preparing alginate fibre according to the present invention suitably comprises contacting one or more medicament with alginate fibre, or a suspension of the alginate, so as to affect uptake of the medicament into the structure of the resultant alginate fibre at a level of at least 10% by weight, based on the weight of the fibre.

The medicament or medicaments may aptly be incorporated into the structure of a mixed salt alginate, by suspending the alginate in deionised water and adding the medicament to the suspension. The above is generally followed by stirring for 6 to 10 hours, typically 8 hours, and separation of the fibre by filtration. Aptly the filtrate is washed with a drying solvent, such as acetone, and optionally dried in air.

Figure 6:
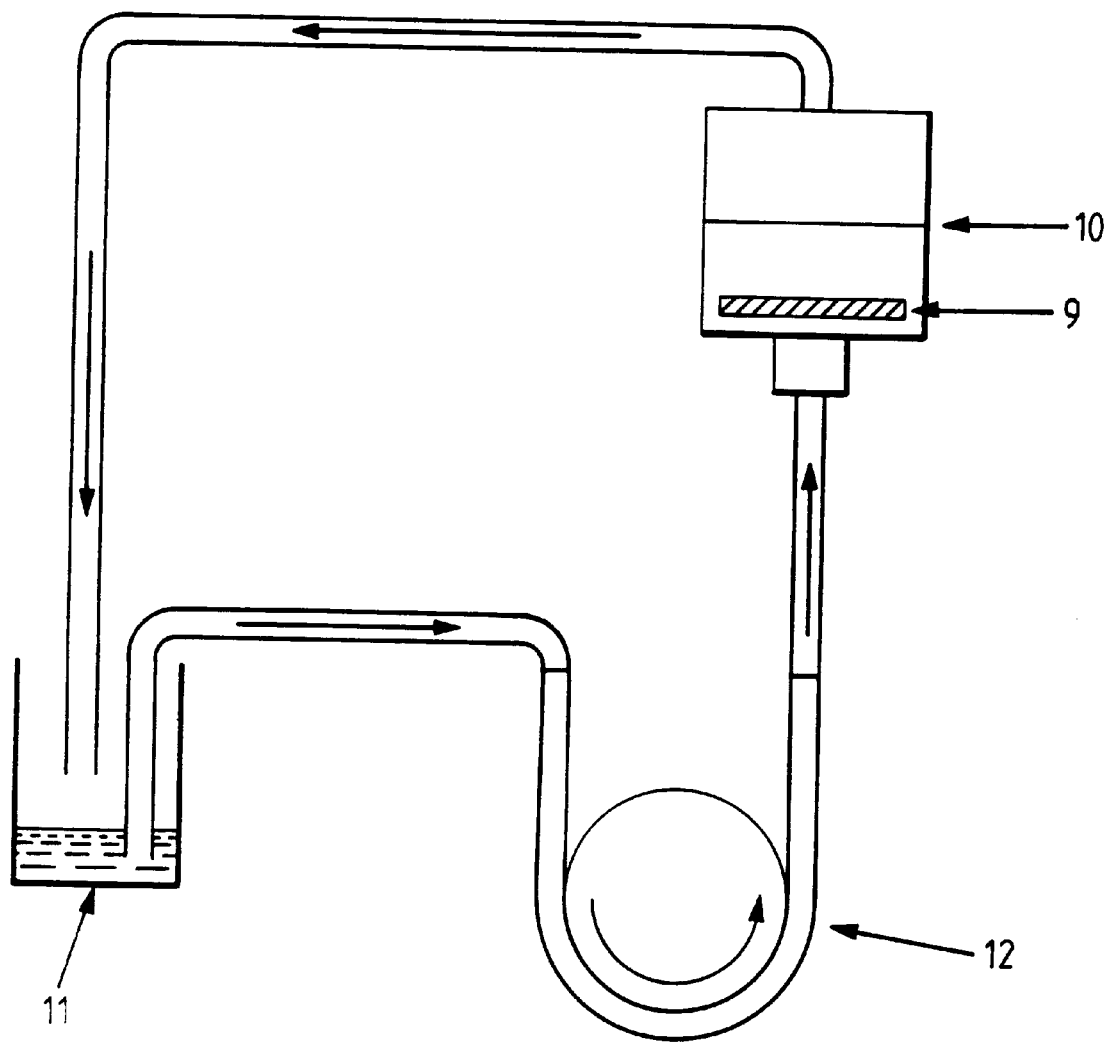
FIG. 6 shows a recirculation system suitable for use in a process for making fibres according to the invention.

Alternatively, the medicament or medicaments can be incorporated into the structure of a mixed salt alginate by recirculating a solution of the medicament or its salt through a pad of alginate fibre, suitably employing a recirculation system as shown herewith in FIG. 6 described in further detail in the Examples. Aptly a buffered solution of a medicament is circulated through a pad of algiante fibre for 3 to 5 hours, typically 4 hours. The fibres are then removed, washed and dried in air.

TEST METHOD 1

Figure 5:
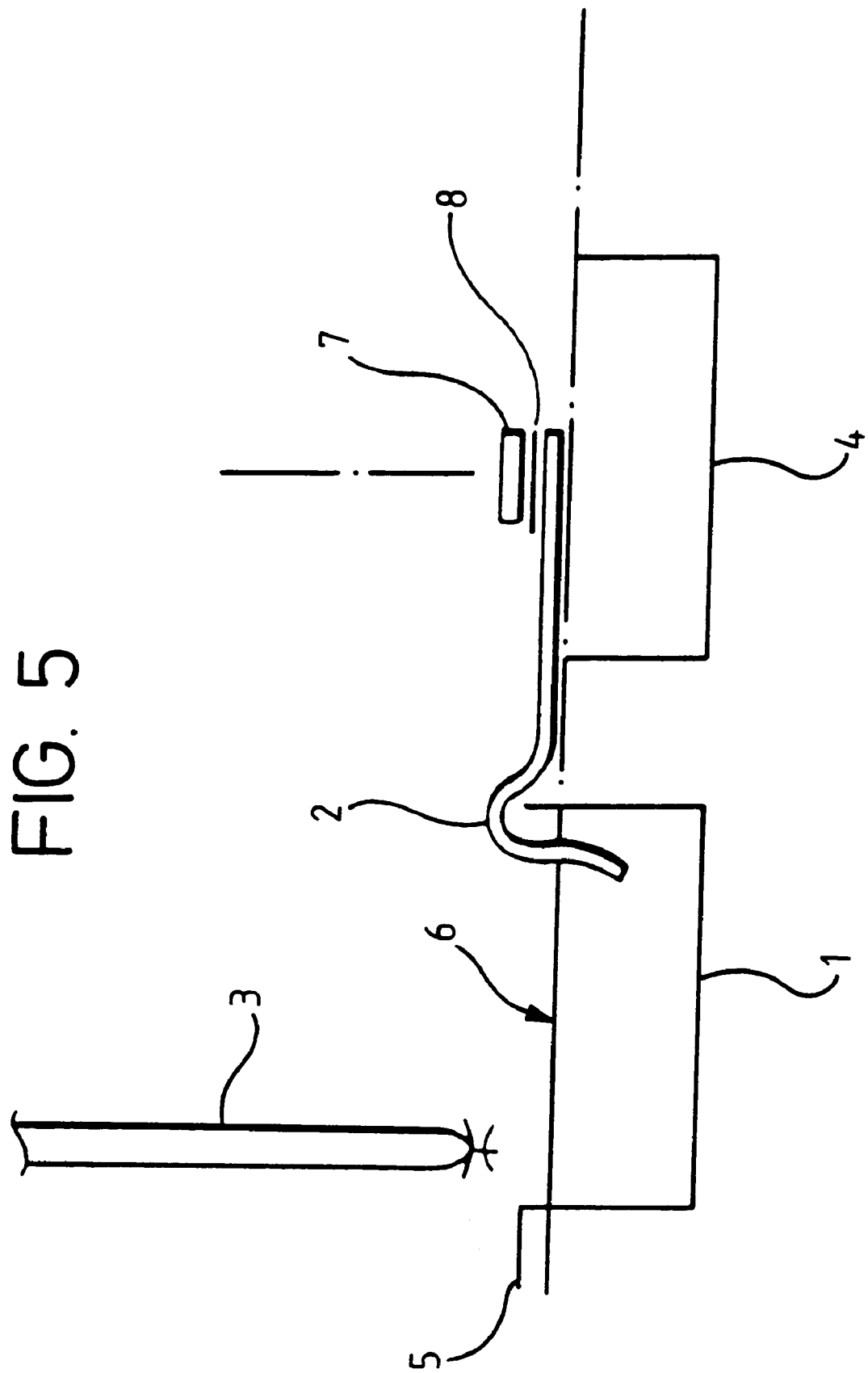
FIG. 5 shows aparatus suitable for determining absorbency.

The apparatus used in the determination of absorbency is depicted in FIG. 5, and consists of water bath 1 containing a 0.9% (w/w) aqueous saline solution, or deionised water, absorbent strip 2, burette 3, top-pan balance 4 and overflow 5.

The thickness of the absorbent strip 2 is substantially equivalent to that of the dressing 7. The filter paper 8 has substantially the same planar dimensions as the dressing 7, but not necessarily the same thickness.

Figure 4:
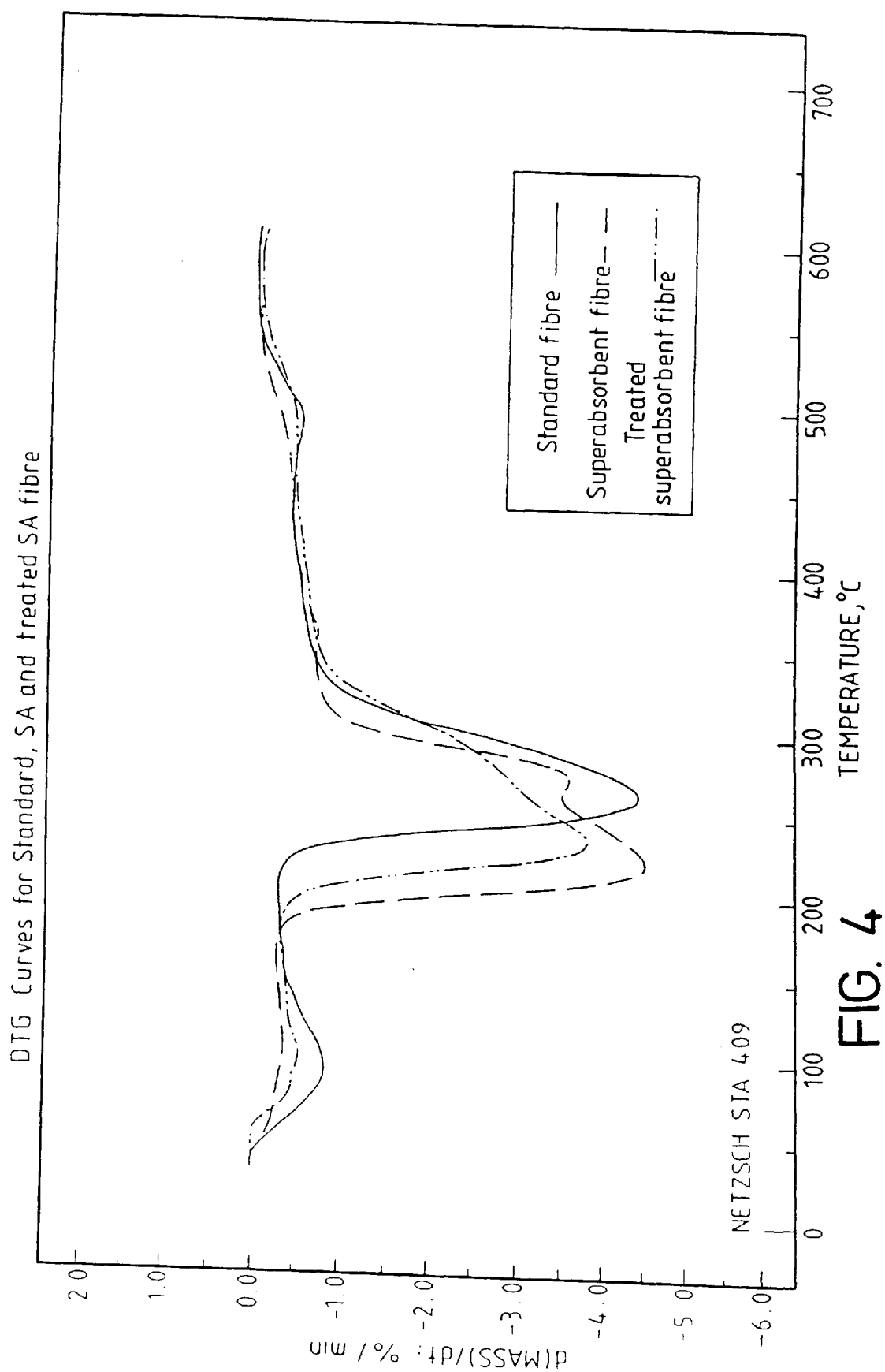
FIG. 4 shows the thermogravimetric analysis of a conventional fibre, a high absorbency fibre according to this invention and such a fibre treated with calcium ions.

The apparatus is set up with the surface 6 of the saline solution or water level with the top surface of the top-pan balance 4. The flow of liquid from the burette 3 is then adjusted to approximately 1.5 ml per minute. The absorbent strip 2 is then saturated and placed between the bath 1 and the balance 4, as depicted in FIG. 1. The balance 4 is then tared. A weighed dressing 7 and filter paper 8 (cut to size) is positioned as depicted in FIG. 4. Care must be taken to ensure that the edge of the absorbent strip 2 furthest away from the water bath 1 does not extend beyond the corresponding edge of the dressing 7, as shown in FIG. 4.

After six minutes the weight shown on the balance 4 is recorded. The dressing 7 and filter paper 8 are then removed and any residual weight on the balance 4 noted.

Absorbency is determined on the basis of the following equation:

$$\begin{matrix} \text{Weight} \\ \text{of} \\ \text{liquid} \\ \text{absorbed} \end{matrix} = \begin{matrix} \text{total} \\ \text{weight} \\ \text{on} \\ \text{balance} \end{matrix} - \begin{bmatrix} \text{dry} & \text{weight} & \text{residual} \\ \text{weight} & \text{of} & \text{weight on} \\ \text{of} & + \text{saturate} & + \text{balance} \\ \text{dressing} & d \text{ filter} & \\ & \text{paper} & \end{bmatrix}$$

TEST METHOD 2

The Tanδ value of a fibre was determined by using a Thurlby Thandor TG502 sweep/function generator, a Tectronics 2212 digital storage oscilloscope and a capacitance test cell (plate area 16 square centimeters and fitted with a 22KΩ resistor). The material to be tested was placed in a small engineers vice and the vice closed. The distance between the plates was measured using a vernier calliper and the earth connection made between the vice and the earth terminal of the capacitance test cell. The function generator and oscilloscope were then connected and the amplitude of the applied sinusoidal voltage measured together with the voltage drop across the resistor and the phase angle between the applied voltage signal and current. The frequency of the applied field was then altered and the measurements repeated for many points in the range 5 mHz to 5 MHZ.

The following non-limiting Examples are intended to illustrate the present invention.

Example 1 describes preparation of a mixed salt alginate suitable for incorporation of a medicament into the structure of the fibre to produce alginate fibres according to the present invention. Examples 2 and 3 describe alternative methods of preparing alginate fibre according to the present invention.

EXAMPLE 1

Calcium alginate fibres were spun from a dope solution containing 4 to 6% sodium alginate employing conventional techniques, and 4 g of the resultant calcium alginate fibres were immersed in 1 M hydrochloric acid (1 liter) for 20–30 seconds. The degree of acid conversion was determined from the relative intensities of the peaks at 1720 $cm^{-1}$ and 1600 $cm^{-1}$ in the infrared spectrum, to ensure that the degree of conversion was in excess of 95%. The fibre was then washed with water and immersed in saturated saline solution (2 liters). The fibre was then chopped to the required staple length. After cutting to the appropriate length the fibre was dispersed into a stirring vessel containing deionised water (2 liter). The fibres were washed in a stream of running water until they swelled to their maximum extent and no sodium chloride could be detected in the eluent. Sodium carbonate solution (0.1M) was then added in 1 ml aliquots whilst monitoring the pH and conductivity of the medium. Care was taken to ensure that the pH did not exceed 6.5. After the addition of approximately 12 mls of sodium carbonate solution (conductivity meter reading between 180 and 200 micro siemens), the material was filtered and dried with acetone followed by air drying.

The product was re-suspended in water (200 $cm^3$) and filtered through a Buchner funnel. Three aliquots (50 $cm^3$) of calcium chloride solution (0.1M) were then slowly filtered through the pad followed by washing with water (200 $cm^3$). The pad was removed and the calcium/sodium content determined by atomic absorption spectrometry (99% calcium, 1% sodium). The pad was then air dried at room temperature.

Absorbency is determined on the basis of the following equation:

$$\text{Weight of liquid absorbed} = \text{total weight on balance} - \left[\begin{array}{c}\text{dry weight of dressing} + \text{weight of saturated filter paper} + \text{residual weight on balance}\end{array}\right]$$

EXAMPLE 2

Alginate fibre (5 g) as prepared in Example 1 was suspended in deionised water (80 cm$^3$). 3 g of protease (crude from bovine pancreas) was added dropwise whilst stirring vigorously. Stirring was continued for 8 hours. The solid fibres were then separated by filtration and the filtrate washed with 3 aliquots of acetone (100 cm$^3$) each. The product was then air dried, and contained 60% by weight of protease.

EXAMPLE 3

Alginate fibre 9 prepared as in Example 1 (0.4 g) was placed in a filter holder 10 and filter holder 10 connected to the recirculating system shown in FIG. 6. TRIS-HCl buffer (pH 7.2, 0.2 cm$^3$) was added to water (30 cm$^3$) and placed in a reservoir 11 and a pump 12 set to circulate at approximately 2 cm$^3$ per minute.

0.3 g of protease (crude from bovine pancreas) dissolved in the minimum quantity of water was added dropwise to reservoir 11, whilst recirculating, over a period of 4 hours. Recirculation was continued for a further 4 hours. The pad was them removed, washed in water (20 cm$^3$), air dried and contained 75% by weight of protease.

EXAMPLE 4

Tan$\delta$ values were measured according to Test Method 2 above for a range of fibre samples. The results were as follows:

| Fibre | Peak 1 Hz | Peak 2 Hz | Peak 3 Hz |
| --- | --- | --- | --- |
| KALTOSTAT[1] | 6449 | 1000 | 896 |
| KALTOGEL[2] | 578 | 416 | 46 |
| KALTOSTAT acid treated, neutralised and dried. | 2929 | 541 | 54 |
| Fibre prepared as in Example 1. | 0.056 | 0.018 | — |
| As above, treated with calcium ions[3] | 5.412 | 2.928 | 0.464 |

[1] commercially available calcium sodium alginate of high guluronate content
[2] commercially available calcium sodium alginate of high malluronate content
[3] the treatment comprised washing the fibres with three 2M CaCl$_2$ solutions each 200 ml per 1.5 g of fibre followed by washing three times with 200 ml of deionised water.

We claim:

1. Alginate fibres comprising at least one medicament incorporated into the structure thereof, the medicament being present at a level of at least 10% by weight, based on the weight of the alginate fibre with no incorporated medicament, and wherein the fibres are characterized by having two maxima in a plot of the first order derivative of percentage weight loss of the fibre with temperature against temperature in the range of 100 to 400° C.

2. Alginate fibres as claimed in claim 1 wherein the medicament is present at a level of at least 30% by weight, based on the weight of the alginate fibres with no incorporated medicament.

3. Alginate fibres as claimed in claim 1 wherein the medicament is selected from the group consisting of: antibacterial agents; gluconate or hydrochloride salts; nisin; sulphonamide derivatives; antiprotozoal agents; antifungal agents; phenothiazine derivatives; nucleosides; hormones; proteases; antibiotics; and anti-inflammatory agents.

4. Alginate fibres as claimed in claim 1 wherein the fibres are characterised by having two maxima in a plot of the first order derivative of percentage weight loss with temperature against temperature in the range 200 to 300° C.

5. Alginate fibres as claimed in claim 1 wherein the fibres are made by a process comprising the following steps:
   (1) treating alginate fibres with a suitable acid so as to produce fibres comprising approximately 90–98%, alginic acid fibres;
   (2) treating the alginic acid fibres with a saturated aqueous solution of mono- or divalent cations;
   (3) washing the fibres with water until imbibition of water by the fibres has effectively ceased;
   (4) treating the fibres with a source of a cation capable of forming a water-soluble alginate salt; and
   (5) contacting the fibres with one or more medicaments so as to affect uptake of the medicament into the structure of the fibre.

6. Alginate fibres as claimed in claim 5 wherein the alginate fibres in step (1) are calcium alginate.

7. Alginate fibres as claimed in claim 6 wherein other ions are included after or during step (4).

8. Alginate fibres as claimed in claim 5 wherein the fibres comprise hyaluronic acid or a pharmaceutically acceptable salt thereof.

9. Alginate fibres as claimed in claim 1 wherein the fibres are characterised by having a glass transition range of less than 30° C.

10. Alginate fibres as claimed in claim 1 wherein the fibres are characterised by having a Tan$\delta$ value in the range from 0 to 15 Hz.

11. Alginate fibres as claimed in claim 1 wherein the fibres have an absorbency of at least 40.0 grams of deionized water per gram of fibres.

12. Alginate fibres as claimed in claim 1 wherein the fibres have an absorbency of at least 60 times their own weight of deionized water.

13. A method of treating a wound comprising the steps of applying a wound dressing comprising alginate fibre to a wound environment, the fibre comprising at least one medicament incorporated into the structure thereof, the medicament being present at a level of at least 10% by weight, based on the weight of the alginate fibre without incorporated medicament, and wherein the fibres are characterized by having two maxima in a plot of the first order derivative of percentage weight loss of the fibre with temperature against temperature in the range of 100 to 400° C.

14. A method of treating a wound as claimed in claim 13 wherein the fibres in the dressing are applied in a wet state.

15. A method as claimed in claim 13 wherein the dressing is applied to the wound for a period selected from one to sixteen days.

16. An alginate fabric formed in whole or in part from alginate fibres, said fibres comprising at least one medicament incorporated into the structure thereof, the medicament being present at a level of at least 10% by weight, based on the weight of the alginate fibre with no incorporated medicament, and wherein the fibres are characterized by having two maxima in a plot of the first order derivative of percentage weight loss of the fibre with temperature against temperature in the range of 100 to 400° C.

17. A wound dressing formed in whole or in part from alginate fibre comprising at least one medicament incorporated into the structure thereof, the medicament being present at a level of at least 10% by weight, based on the weight of the alginate fibre with no incorporated medicament, and wherein the fibres are characterized by having two maxima in a plot of the first order derivative of percentage weight loss of the fibre with temperature against temperature in the range of 100 to 400° C.

18. A wound dressing as claimed in claim 17 comprising one or more further absorbent layers arranged on either side of the alginate fibres.

19. An implantation composition comprising an alginate fibre comprising at least one medicament incorporated into the structure thereof, the medicament being present at a level of at least 10% by weight, based on the weight of the alginate fibre with no incorporated medicament, and wherein the fibres are characterized by having two maxima in a plot of the first order derivative of percentage weight loss of the fibre with temperature against temperature in the range of 100 to 400° C.

* * * * *